United States Patent
Saltzstein et al.

(10) Patent No.: US 6,727,814 B2
(45) Date of Patent: Apr. 27, 2004

(54) SYSTEM, METHOD AND APPARATUS FOR SENSING AND COMMUNICATING STATUS INFORMATION FROM A PORTABLE MEDICAL DEVICE

(75) Inventors: William E. Saltzstein, Woodinville, WA (US); Paul S. Tamura, Seattle, WA (US); Richard C. Nova, Kirkland, WA (US); Shawn R. Bertagnole, Lake Stevens, WA (US)

(73) Assignee: Medtronic Physio-Control Manufacturing Corp., Redmond, WA (US)

( * ) Notice: Subject to any disclaimer, the term of this patent is extended or adjusted under 35 U.S.C. 154(b) by 198 days.

(21) Appl. No.: 09/963,100

(22) Filed: Sep. 24, 2001

(65) Prior Publication Data

US 2003/0058097 A1 Mar. 27, 2003

(51) Int. Cl.[7] .......................... H04Q 1/30; G08B 1/08; A61B 5/00
(52) U.S. Cl. ............ 340/531; 340/539.11; 340/539.12; 340/539.24; 340/573.1; 340/555; 340/525; 600/300; 128/903; 706/924
(58) Field of Search ................... 340/531, 539, 340/573.1, 679, 3.43, 815.45, 815.47, 525, 539.12, 539.11, 539.17, 539.24; 706/924; 600/300, 509; 359/110, 143, 144; 128/903, 904; 250/200, 491, 227.11, 227.14

(56) References Cited

U.S. PATENT DOCUMENTS

| | | |
|---|---|---|
| 4,622,540 A | 11/1986 | Guscott et al. |
| 4,749,853 A | 6/1988 | Salim |
| 4,916,439 A | 4/1990 | Estes et al. |
| 5,015,840 A | 5/1991 | Blau |
| 5,130,532 A | 7/1992 | Clemens |
| 5,243,183 A | 9/1993 | Barron, Jr. et al. |
| 5,419,336 A | 5/1995 | Margison |
| 5,424,532 A | 6/1995 | Occheto et al. |
| 5,703,562 A | 12/1997 | Nilsen |
| 5,760,389 A | 6/1998 | Biasi |
| 5,805,062 A | 9/1998 | Pearlman |
| 5,959,529 A * | 9/1999 | Kail, IV ..................... 340/539 |
| 5,967,975 A * | 10/1999 | Ridgeway ..................... 600/300 |
| 5,973,594 A | 10/1999 | Baldwin et al. |
| 5,998,785 A | 12/1999 | Beck et al. |
| 6,157,313 A | 12/2000 | Emmermann |
| 6,221,010 B1 * | 4/2001 | Lucas ........................ 600/300 |
| 2003/0025602 A1 * | 2/2003 | Medema et al. ............ 340/531 |

* cited by examiner

Primary Examiner—Donnie L. Crosland
(74) Attorney, Agent, or Firm—Shumaker & Sieffert, P.A.

(57) ABSTRACT

A system, method and apparatus for obtaining status information from a portable medical device and communicating said status information to a remote system or user. In one embodiment, the system comprises a sensing device that comprises an optical receiver for receiving status information from at least one status indicator of the portable medical device. The optical receiver is positioned in sufficient proximity to the status indicator to allow optical communication between the optical receiver and the status indicator. A circuit couplable to the optical receiver communicates the status information represented by the status indicator to the remote system or user. In another embodiment, the sensing device comprises a microphone to receive audible status signals from the portable medical device. In yet another embodiment, the sensing device is mounted to a housing, which allows sensing device to sense the status information of an enclosed portable medical device.

42 Claims, 6 Drawing Sheets

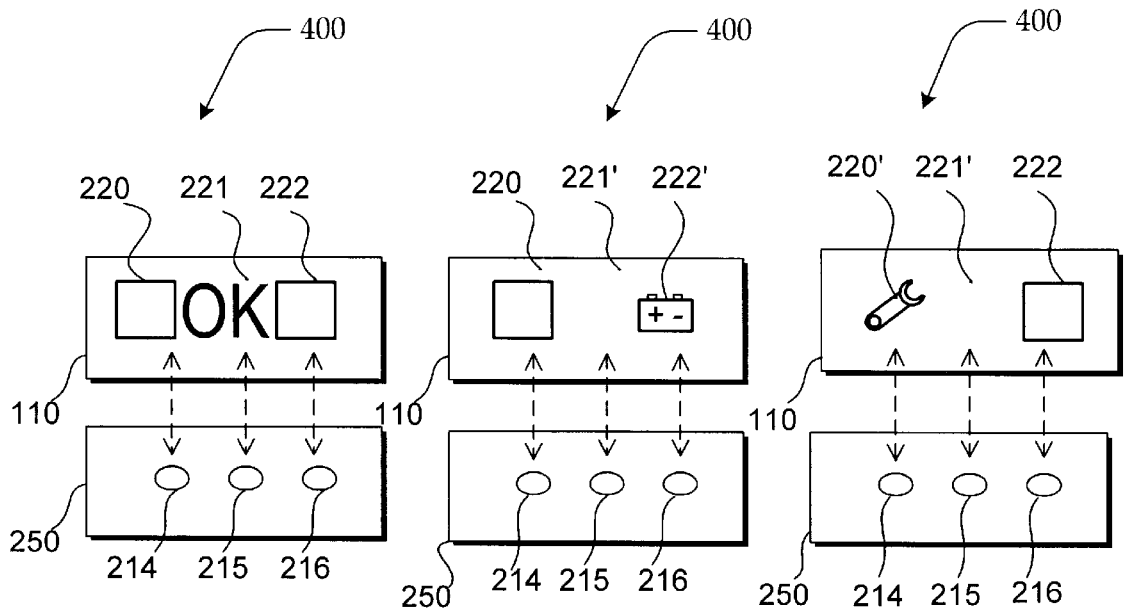
*Fig.4A.*  *Fig.4B.*  *Fig.4C.*
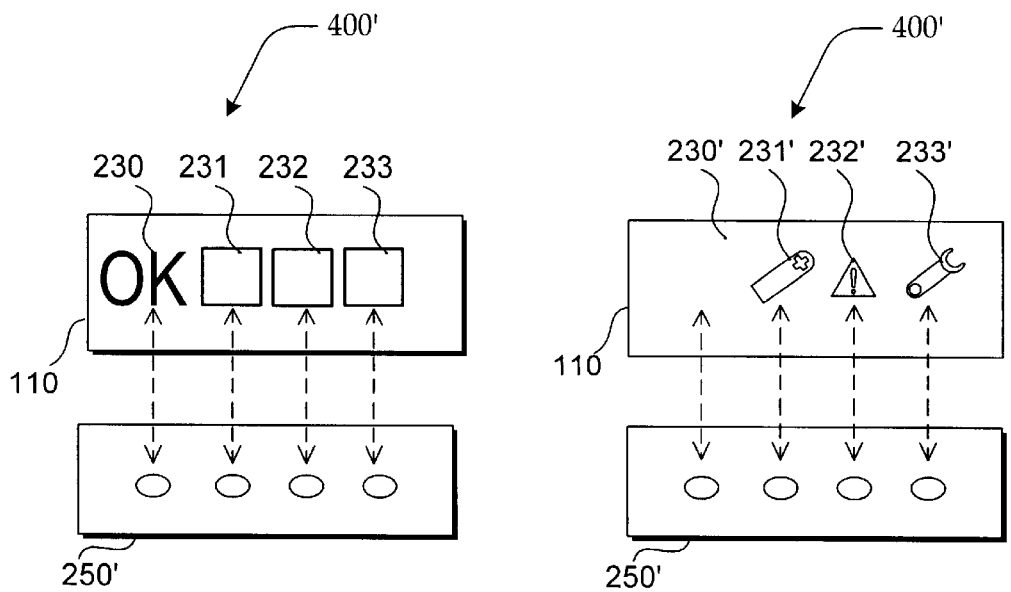
*Fig.4D.*  *Fig.4E.*

SYSTEM, METHOD AND APPARATUS FOR SENSING AND COMMUNICATING STATUS INFORMATION FROM A PORTABLE MEDICAL DEVICE

FIELD OF THE INVENTION

The present invention relates to portable medical devices, and more particularly, to a system, method and apparatus for sensing and communicating status information from a portable medical device.

BACKGROUND OF THE INVENTION

Portable medical devices, such as automated external defibrillators (AED's), generally include a status circuit for communicating status information of the portable medical device to a user. In some existing systems, a status circuit of a portable medical device generally includes a visual display, such as a liquid crystal display (LCD) or a light-emitting diode (LED), for providing notice to a user that the portable medical device has a failed or expired internal component, e.g., a low battery, etc. Certain existing systems also include an audible alarm to communicate the status information of the portable medical device to a user.

Although existing status circuits are effective for communicating status information to a user in close proximity to the portable medical device, existing status circuits also present many disadvantages. For instance, when a portable medical device is stored in a cabinet, closet or other like enclosure, the visual display and audible alarm of the device are ineffective in communicating the status information because the device is in a confined location. Because of this drawback, many portable medical devices stored in enclosed areas are not properly maintained when the battery fails or when the device malfunctions.

Status circuits of existing portable medical devices present other communication problems in situations where a portable medical device is integrated into an external computing system. More specifically, the visual and audible alarms utilized in existing portable medical devices do not effectively communicate the device's status information to other external systems, such as a building alarm system. Existing portable medical devices require substantial hardware modifications to retrofit the electronics needed for communicating the device's status information to an external system. For example, a wired or wireless communication circuit may be installed in a portable medical device to facilitate the communication of the device's status information to an external system. Such modifications are generally impractical because of the cost associated with the equipment and services related to the modification.

Accordingly, there is a need for a system and method that allows a portable medical device to effectively communicate its status information when the device is stored in an enclosed area. In addition, there is a need for a system and method that allows a portable medical device to effectively communicate status information with external systems without the need of substantial hardware and/or software modification to the portable medical device.

SUMMARY OF THE INVENTION

The present invention provides a system, method and apparatus for sensing and communicating status information from a portable medical device to a remote computing system and/or user. In one aspect of the present invention, the present invention provides a system that readily adapts to a portable medical device's existing, external status indicators. Generally described, the system, method and apparatus of the present invention detects state changes of a status indicator configured in a portable medical device and electronically communicates the state changes of the status indicator to a remote system, such as a building alarm system. The system of the present invention may also be configured to communicate state changes of the status indicator to a user located at a remote location by generating a visual or audible alarm signal. By the use of the system, method and apparatus of the present invention, a remote system and/or remote user can readily determine if an internal component of a portable medical device has failed or expired. In addition, the remote system and/or user can readily determine if the portable medical device has been deployed, stolen, moved, etc.

In one embodiment, the system comprises a receiver for receiving status information from a visual display of a portable medical device. The receiver is positioned to align with at least one status indicator of the device, such as an LCD, LED, speaker or the like. The system also includes a circuit for controlling the receiver and for providing electronic communication between the receiver and a remote computer system. Accordingly, status signals such as a low battery warning light can be detected by a remote computer system without the requirement of retrofitting electronic components into existing portable medical devices.

In another embodiment, the system of the present invention further comprises audio and visual indicators that relay the status signals of a portable medical device to users and/or other external computing systems.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 4A–4E are illustrations of a status sensing system configured to detect status signals from a visual display of a portable medical device;

DETAILED DESCRIPTION OF THE PREFERRED EMBODIMENT

The present invention provides a system, method and apparatus for sensing and communicating status information from a portable medical device to a remote computing system and/or user. Generally described, the system, method and apparatus of the present invention detects state changes of a status indicator configured in a portable medical device and electronically communicates the state changes of the status indicator to a remote system, such as a building alarm system. The system of the present invention may also be configured to communicate state changes of the status indicator to a user located at a remote location by generating a visual or audible alarm signal.

By the use of the system, method and apparatus of the present invention, a remote system and/or remote user can readily determine if an internal component of a portable medical device has failed or expired. In addition, the remote system and/or user can readily determine if the portable medical device has been deployed, stolen, moved, etc. As described in more detail below, illustrative embodiments of the system, method and apparatus utilize audible and visual indicators to determine a changed status of the portable medical device.

Figure 1:
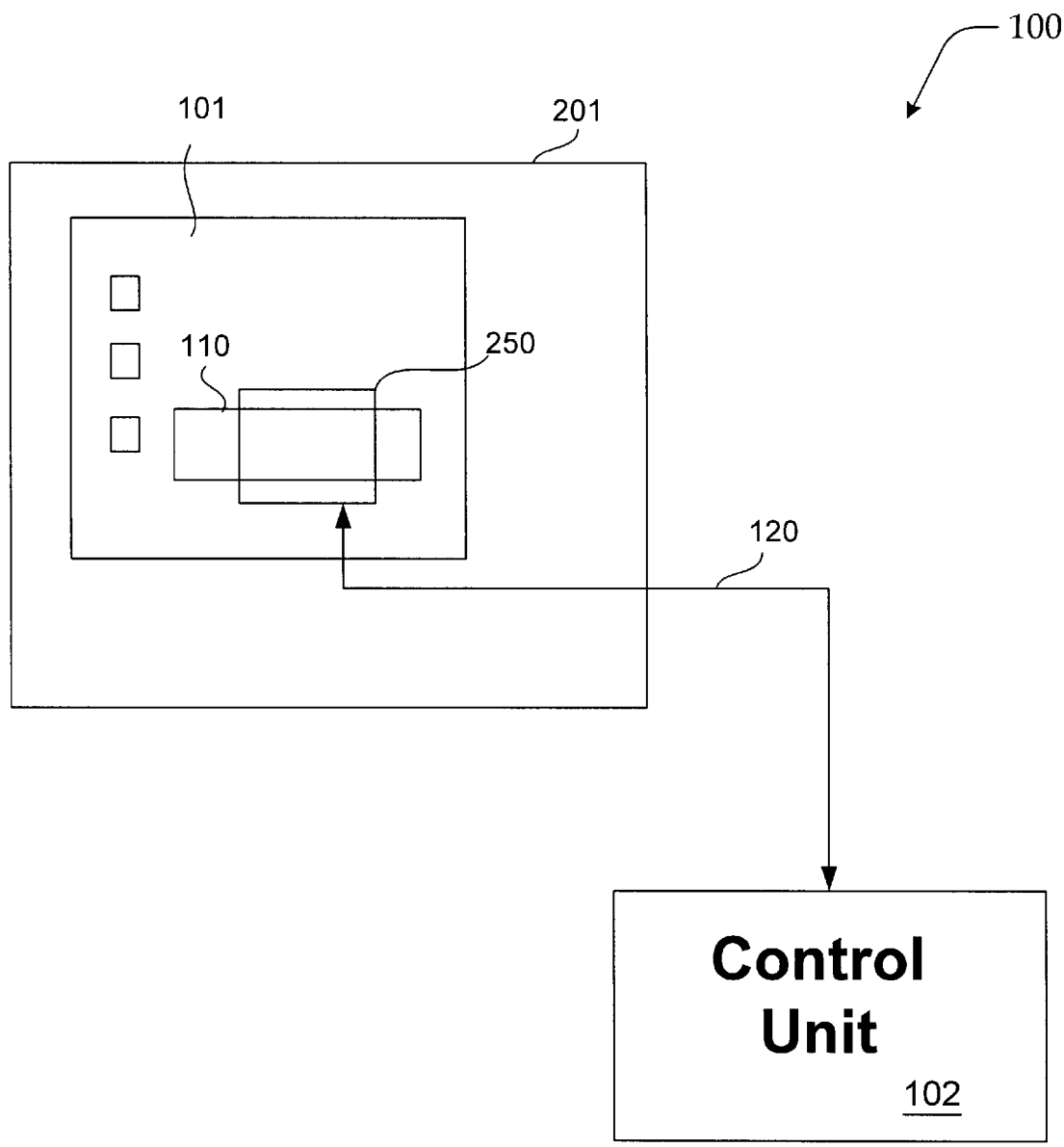
FIG. 1 is a block diagram of one embodiment of a status sensing system for communicating status information from a portable medical device to a control unit.

Referring now to FIG. 1, one embodiment of a status sensing system 100 formed in accordance with the present invention is shown. Generally described, the status sensing system 100 comprises a sensing device 250 that reads and/or receives status signals from a status indicator of a portable medical device 101 positioned in an enclosed area 201, such as a cabinet, closet, car trunk, etc. The sensing device 250 includes communication circuitry that allows the sensing device 250 to communicate the received status signals from the portable medical device 101 to a control unit 102, such as a building alarm system, car alarm system or a remote computer. As will be described in more detail below, the sensing device 250 may comprise one or more optical sensors for detecting visual status indicators from a visual display 110 of a portable medical device 101. In another embodiment, the sensing device 250 may be configured with a microphone for sensing audible signals generated by a speaker of the portable medical device 101. In other embodiments, the sensing device 250 may be configured with any other mechanical or electrical sensor, such as a magnetic or tactile sensor, that detects a state change of a status indicator.

The sensing device 250 and control unit 102 communicate via a communication link 120. The communication link 120 may be in the form of any electronic wired or wireless communication system, such as a two-way radio, wireless telephony system, etc. It will be appreciated that the communications link 120 may utilize any one of a variety of communications media and/or communication protocols or methods to transfer data. Examples of suitable wire communications media/methods include, but are not limited to, public switch telephone networks ("PSTN"), wired digital data networks, such as the Internet or a local area network ("LAN"), co-axial cable, fiber optic cable and the like. Examples of suitable wireless communications media/methods include, but are not limited, wireless telephony including analog cellular, digital personal communications service ("PCS"), short message service ("SMS"), and wireless application protocol ("WAP"). Other suitable wireless communication media/methods include wireless digital data networks, such as IEEE 802.11 wireless LAN ("WLAN"), two-way paging networks, specialized mobile radio systems, infrared, and non-licensed ISM-service communication links, such as Bluetooth. Further, some communication methods, either wired or wireless, include Internet protocol ("IP") addressing. One skilled in the relevant art will appreciate that additional or alternative communication media/methods may be practiced and are considered within the scope of the present invention. Accordingly, those of ordinary skill in the art will appreciate that the communications link 120 may be constructed with commercially available circuitry necessary for the particular type of communication described herein. For example, in the embodiment illustrated in FIG. 1, the communication link 120 may be constructed from components analogous to the electronics used for a two-way radio system commonly used in a home alarm system.

It will be appreciated that portable medical device 101 may be any electronic medical device such as an automated external defibrillator (AED). As known to one of ordinary skill in the art, typical portable medical devices have a user interface that provides a visible, audible and/or other signals to indicate the status of the device. For example, the portable medical device 101 may include a visual display 110 configured to turn on an LED to indicate that the device's battery is low. In another example, the portable medical device 101 monitors a timer in accordance with a maintenance schedule and activates an LCD display when a scheduled maintenance is due. Although these specific examples of status indicators are used for illustrative purposes, the scope of the present invention includes the detection of any signal (visible, audible, tactile, etc.), generated by a portable medical device 101.

As a non-limiting example, the control unit 102 may be in the form of an alarm system that is installed in a commercial or residential building. In one embodiment, the control unit 102 includes the electronic circuitry needed for receiving an electronic signal from the sensing device 250 via a wireless or wired connection. For example, the electronic signal may be generated by the closure of a relay switch. The control unit 102 also relays the status information received from the sensing device 250 to a user or any remote computer system. For example, the control unit 102 may include a light and/or speaker system capable of producing audible and/or visual signals to a user, such as an alarm system attendant. In another example, the control unit 102 produces an electronic signal that translates the status information into a text message or any other computer readable signal. The control unit 102 may then forward the message to another remote system, such as an emergency, e.g., 911, computer aided dispatch (CAD) system. In yet another embodiment, the control unit 102 itself may comprise the computer aided dispatch system.

As shown in the embodiment illustrated in FIG. 1, the sensing device 250 is positioned in relation to the visual display 110 of the portable medical device 101 such that the signals produced by the visual display 110 may be detected by the sensing device 250. As described in more detail below with reference to FIGS. 5 and 6, the sensing device 250 includes a plurality of light sensitive transistors for detecting light signals from one or more visual status indicators of the visual display 110 that change as the status of the portable medical device 101 changes. Each light sensitive transistor on the sensing device 250 is aligned to read individual status indicators from the visual display 110. More specifically, in the embodiment illustrated in FIG. 5, the sensing device 150 is aligned and configured to read signals from a visual display constructed from light-emitting diodes (LEDS). In the embodiment illustrated in FIG. 6, the sensing device 250 is aligned and configured to read signals from a liquid crystal (LCD) visual display. As will be described in more detail below, regardless of the type of display, the sensing device 250 generates and communicates a number of unique electronic signals that differentiate the different status signals received from the visual display 110.

Figure 2A:
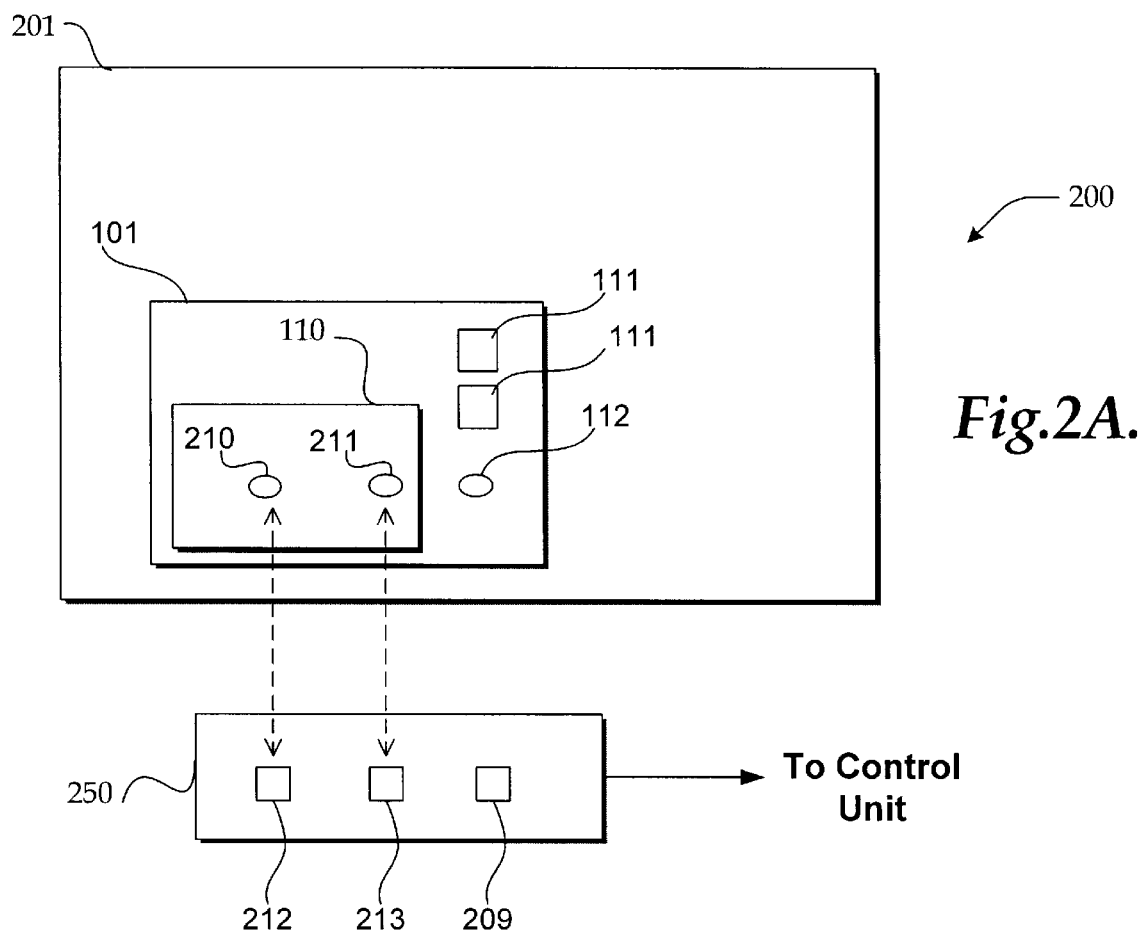
FIGS. 2A–2B are pictorial views of a portable medical device and a status sensing system formed in accordance with the present invention.
Figure 2B:
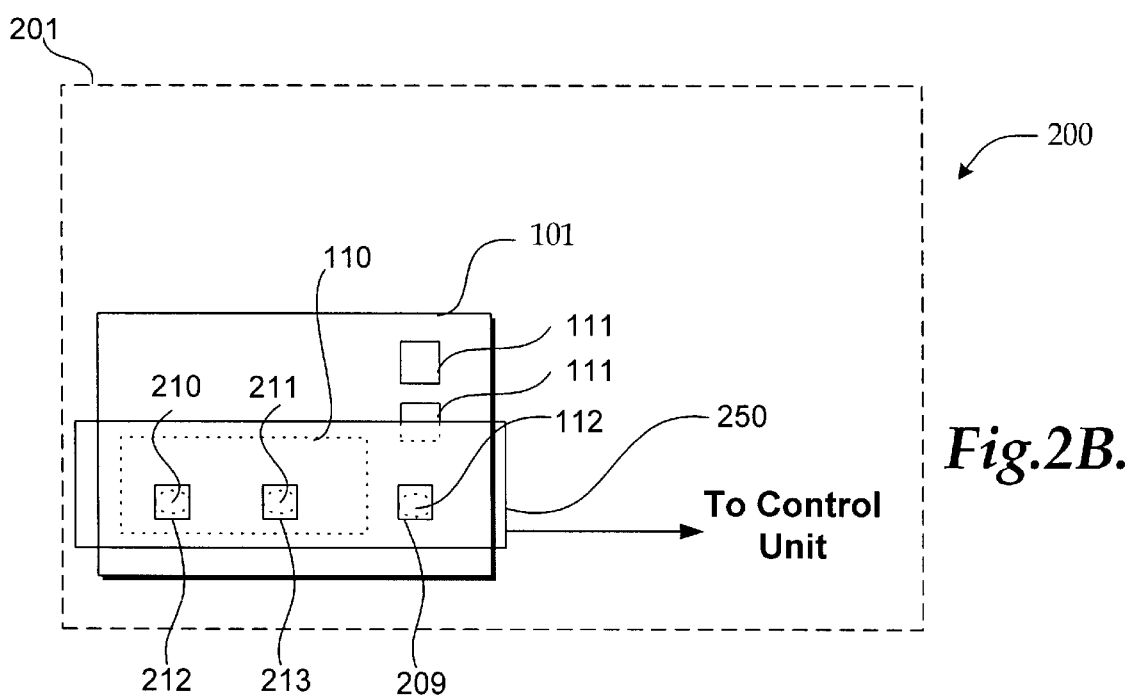

Referring now to FIGS. 2A and 2B, one embodiment of the status sensing system 200 is shown wherein the portable medical device 101 is located in an enclosed area 201. The portable medical device 101 includes a display 110 and a plurality of control buttons 111 used for normal operation of the portable medical device 101. The portable medical device 101 also comprises two visual status indicators 210 and 211 configured on the display 110 for communicating the status, such as a low battery, of the portable medical device 101. In addition, the portable medical device 101 further comprises a speaker 112 for communicating the status of the portable medical device 101 in the form of an audible signal. As can be appreciated by one of ordinary skill in the art, the above-described configurations of the portable medical device are provided for illustrative purposes and not to be construed to limit the scope of the present invention to such embodiments or configurations disclosed herein. For instance, the status sensing system of the present invention may be configured to receive any status signal from a portable medical device regardless of the form of the signal, e.g., electrical, mechanical, magnetic, etc.

Also shown in FIGS. 2A and 2B, the portable medical device 101 is enclosed in a compartment 201. The enclosed area 201 may be any type of enclosure such as a closet, cabinet, carrying case, car trunk or any other like enclosure that muffles the speaker 112 or inhibits the visibility of the visual status indicators 210 and 211. The sensing device 250 is positioned over the audible and visual status indicators 112, 210 and 211, and sized to fit inside the enclosed area 201. As described below, the sensing device 250 is also electronically configured to communicate any state change of the audible and visual status indicators 112, 210 and 211 to any remote system (such as a control unit 102 of FIG. 1) or user.

FIG. 2A illustrates the configuration of a sensing device 250 having two optical sensors 212 and 213 positioned for receiving light signals from the two visual status indicators 210 and 211 of the portable medical device 101. In one embodiment, the optical sensors 212 and 213 are aligned such that the distance between each optical sensor 212 and 213 matches the distance between each visual display 210 and 211. This embodiment allows each optical sensor to receive individual signals from a corresponding status indicator.

Also shown in FIG. 2A, the sensing device 250 also comprises a microphone 209 for receiving audible signals from the speaker 112 of the portable medical device 101. In one embodiment, the sensing device 250 and microphone 209 determine the state of the portable medical device 101 by detecting the presence or absence of an audible signal produced by the speaker 112. In other embodiments, the sensing device 250 can be configured to distinguish various status signals by distinguishing different audible signals. For instance, the sensing device 250 can be configured to monitor the duration of audible signals, or the duration between audible signals, produced by the speaker 112 to determine a particular status or to filter false alarms. In other illustrative examples, the sensing device 250 can distinguish different volumes, tones, waveforms, frequencies, etc., to determine a particular status. Although these methods of distinguishing audible status signals are disclosed in these examples, any other method of distinguishing audible signals also fall within the scope of the present invention.

As shown in FIG. 2B, in normal operation of the status sensing system 200, the sensing device 250 is positioned in relation to the portable medical device 101 such that the optical sensors 212 and 213 are respectively positioned over the visual status indicators 210 and 211. In one embodiment, the sensing device 250 is positioned such that each optical sensor 212 and 213 is configured for receiving individual light signals from each corresponding visual status indicator 210 and 211 without substantial interference from external light sources. It is also preferred that the sensing device 250 is configured such that it does not interfere or actuate the control buttons 111 of the portable medical device 101. Also shown in FIG. 2B, when the sensing device 250 is positioned near the portable medical device 101, the microphone 209 is positioned near the speaker 112. In one embodiment, the sensing device 250 is affixed to the portable medical device 101 by the use of an adhesive, Velcro, elastic band, or any other like material that holds the sensing device 250 in place while also allowing trouble-free removal of the sensing device 250.

Figure 3:
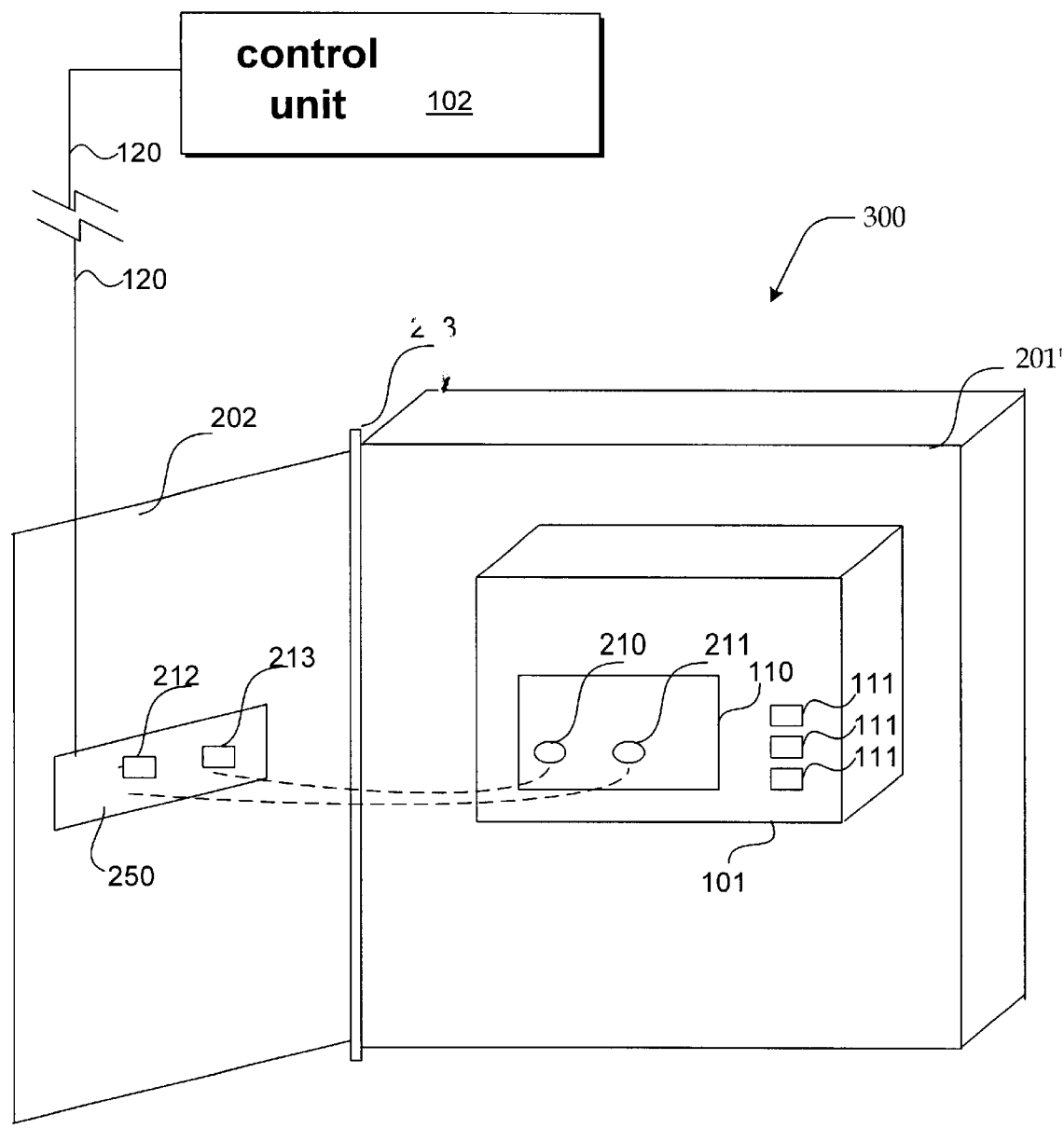
FIG. 3 is a perspective view of one embodiment of a status sensing system adapted for communicating status information of a portable medical device stored in an enclosed area.

Referring now to FIG. 3, an enclosed portable medical device 300 is shown. In this illustrative example, the portable medical device 300 is enclosed in a cabinet 201' having a movable door 202 attached by a hinge 203. The door 202 of the cabinet 201' is configured to open and close about the hinge 203 such that when the door 202 is in a closed position, the door 202 secures the portable medical device 300 inside of the cabinet 201'. As shown in FIG. 3, the sensing device 250 is affixed to the door 202 such that when the door 202 is in a closed position, the individual optical sensors 212 and 213 respectively align with a corresponding visual status indicator 210 and 211 of the portable medical device 101. The sensing device 250 can be affixed to the door 202 by the use of any adhesive or mechanical device sufficient to hold the sensing device 250 in place while the door 202 is in motion.

Also shown in FIG. 3, the sensing device 250 is electronically configured to provide a communication link 120 that allows the sensing device 250 to transmit the status information of the portable medical device 101 to a control unit 102. As described above, the control unit 102 may be an alarm system such as those typically utilized in a commercial or residential building or a computer-aided dispatch system. In another embodiment, and as described in more detail below with reference to FIG. 6, the control unit 102 may also comprise an electronic device capable of producing a visual and/or audible alarm.

Referring now to FIGS. 4A–4E, two sensing systems 400 and 400' are shown. The following describes the general structure and operation methods of two types of visual status indicators of a portable medical device 101. A description of two sensing devices configured for each type of visual status indicator is then provided.

FIGS. 4A–4C illustrate one configuration of a visual display 110 having three individual status indicators 220–222 constructed from a light-emitting electronic device such as a light-emitting diode (LED). In this embodiment, each individual status indicator 220–222 comprises an LED and an optical device such as a plastic transparency, which reveals a status icon when the LED is illuminated. More specifically, depending on the status of the portable medical device 101, e.g., when the device needs maintenance, the LED may turn on or off to produce an illuminated icon 220' or a shaded area 220.

In another embodiment, each of the three individual status indicators 220–222 of FIGS. 4A–4C comprises two individual light-emitting diodes. Accordingly, one status indicator may be configured to illuminate a first color of light via the first LED and a second color of light via the second LED. For example, in the case of a low battery condition, the portable medical device 101 may activate a red or green LED to communicate the device's battery condition. When the device battery is not low, the portable medical device may activate a green LED to indicate the same. In this configuration, the green LED illuminates a plastic transparency to reveal the shape of a square box 220 as shown in FIG. 4A. When the battery status of the portable medical device 101 changes, the red LED of the first indicator 220 is activated and the green LED is turned off. In the changed state of the first indicator 220, the light emitted from the red LED illuminates the plastic transparency in the shape of low battery icon 220' as shown in FIG. 4B.

In the example shown in FIG. 4C, the light emitted from the red LED illuminates a plastic transparency that exposes an icon indicating the need for maintenance in the shape of a wrench 220'. Accordingly, the illumination of a square block 220 by the green LED indicates that the portable medical device 101 is in normal operation. As known to one of ordinary skill in the art, optical devices for exposing an illuminated icon can be constructed of a shaped plastic transparency or any other like material. Other exemplary status indicators having other icon shapes such as a text message 221 and a battery 222' are also depicted in FIGS. 4A–4C. Thus, it will be appreciated by those of ordinary skill in the art that the visual display may include any number, type or combination of status indicator without departing from the spirit and scope of the present invention. For example, the visual display can include only one status indicator or it may include as many status indicators as the manufacturer desires. Further, each status indicator may comprise one, two or any other number of LEDs for illumination. Further, in some embodiments the status indicator may simply comprise the LED(s) itself without any type of optical device for illuminating an icon. Accordingly, the mere color of the LED would indicate the status of the device. Finally, visual display 110 may comprise a plurality of status indicators of different types. Accordingly, it is only necessary that the sensing device 250 be configured to correspond to the number, type and combination of status indicators in order for the sensing system to be complete.

In this regard, sensing device 250 detects state changes of the light-emitting status indicators 220–222 described in FIGS. 4A–4C. Accordingly, the sensing device 250 comprises a plurality of optical sensors 214–216 that are aligned to receive the light signals from the status indicators 220–222. As shown in FIGS. 4A–4C, the first optical sensor 214 is aligned to receive the light emitted from the first status indicator 220. Similarly, the second optical sensor 215 is aligned to receive the light emitted from the second status indicator 221, and the third optical sensor 216 is aligned to receive the light emitted from the third status indicator 222. As described in more detail below with reference to FIG. 5, each optical sensor 214–216 is configured with a light sensitive transistor capable of sensing light from the status indicators 220–222. In another embodiment, each optical sensor 214–216 includes a light sensitive transistor capable of sensing light at a specific wavelength, thus allowing the sensing device 250 to distinguish green, red or other light signals emitted by the visual status indicators 220–222. In addition to the optical sensors 214–216, the sensing device 250 includes with accompanying electronics that allow the sensing device 250 to generate an electronic signal when the light-sensitive transistors of the optical sensor receive a light signal from the status indicators. The accompanying electronics also transmit the generated electronic signal to a remote system, such as the control unit 102 via a communication link 120. As known to one of ordinary skill in the art, the accompanying electronics for generating and communicating the electronic signal from the light-sensitive transistors may be constructed from generally known solid-state components.

Referring now to FIGS. 4D–4E, an embodiment of a visual display 110 having four individual status indicators 230–233 is shown and described below. The four individual status indicators 230–233 include an LCD that generates a shaded area 230–233 positioned over a back plane having several painted icons 230'–233'. In this embodiment, the text message 230 and shaded blocks 231–233 are generated when the LCD is activated. When the LCD is not activated, the LCD is transparent, thus exposing the painted icons 230'–233' positioned below the LCD. As shown in FIG. 4E, several icons are painted in the second, third, and fourth status indicators 231'–233' signifying a low battery, component failure, or a maintenance schedule alarm. The back plane of the first status indicator 230' does not include a painted icon. Such blank areas are configured for an LCD block configured for displaying a text message, such as the "OK" text message 230 of FIG. 4D. The LCD controlling each of the status indicators 230–233 independently toggles the LCD between the blackened state as shown in FIG. 4D to a transparent state thus displaying the painted icons as shown in FIG. 4E.

Similar to the embodiment of FIGS. 4A–4C, the sensing device 250' of FIGS. 4D–4E is configured with the plurality of optical sensors that are each aligned to sense light signals from each status indicator 230–233. In this embodiment, and as described in more detail below with reference to FIG. 6, the sensing device 250' also comprises an LED configured to create a light reflection from each status indicator 230–233. The reflected light produced by the LEDs allow the optical sensors of the sensing device 250' to detect state changes of each LCD status indicator 230–233.

As can be appreciated by one of ordinary skill in the art, the examples of FIGS. 4A–4E are provided for illustrative purposes and are not intended to limit the scope of the present invention to the illustrative examples disclosed herein. More specifically, the status indicators of FIGS. 4A–4E may be in the form of any electrical, electromechanical, mechanical, tactile, or any other mechanism that communicates a status. For example, one visual status indicator of a portable medical device may in the form of a mechanical switch configured to expose different colors on a display to indicate a particular status. In such an embodiment, a solenoid may be mechanically attached to an apparatus having multiple colors, and depending on the position of the solenoid, individual colors of the apparatus can be displayed to indicate a particular status. In another example, the status indicator of a portable medical device may be in the form of an electro-magnetic device configured to expose different colors on a display to indicate a particular status. Accordingly, a sensing device of the present invention may be configured to detect the device's status from such a visual status indicator.

Figure 5:
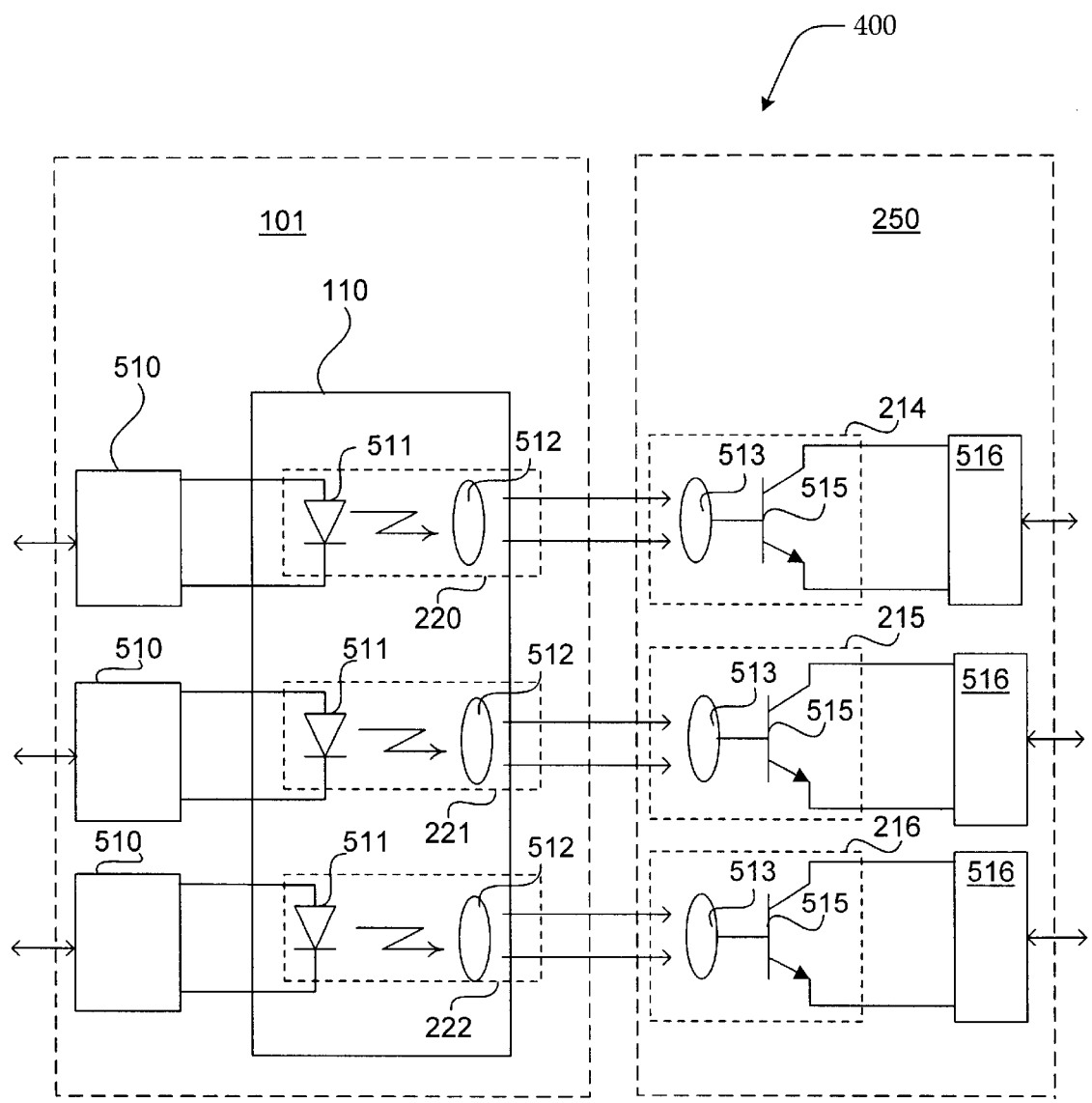
FIG. 5 is a block circuit diagram of one embodiment of a status sensing system configured for reading state changes of a light-emitting display.

Referring now to FIG. 5, a block circuit diagram of one embodiment of a status sensing system 400 is shown. The block circuit diagram of FIG. 5 illustrates the sensing system 400 described above with reference to FIGS. 4A–4C. In addition, FIG. 5 illustrates the visual display 110 of a portable medical device 101 having a plurality of light-emitting status indicators 220–222. As shown in FIG. 5, the sensing device 250 is configured to detect changes in the light signals generated by the LEDs 511 in the status indicators 220–222 of a portable medical device 101.

FIG. 5 illustrates the major components of a sensing device 250 and a visual display 110 necessary for one implementation of the present invention. The following discussion is intended to describe one suitable environment in which the invention may be implemented. Those of ordinary skill in the art will appreciate that the visual display and sensing device may include more components than those shown in FIG. 5. However, it is not necessary that all of these generally conventional components be shown in order to disclose an enabling disclosure for practicing the present invention.

As described above with reference to FIGS. 4A–4C, the status indicators 220–222 of the portable medical device 101 may emit one or more colors of light to communicate a particular status of the portable medical device 101. As shown in FIG. 5, each status indicator 220–222 comprises an LED 511 and an optical focusing device 512 for directing the emitted light away from the portable medical device 101. In addition, each status indicator 220–222 is connected to a control circuit 510 for activating each LED 511. Also shown in FIG. 5, the control circuit 510 is electronically connected to the various components internal to the portable medical device 101 for sensing the status of the components, such as the battery level, maintenance schedule, etc. As described above, the control circuit 510 indicates a status change on one or more status indicators 220–222 when a status of a device component changes.

Although FIG. 5 depicts a visual display 110 having three status indicators 220–222, the present invention may include other embodiments in which the visual displays have any number of status indicators. In addition, as described above with reference to FIGS. 4A–4C, the status indicators may also include a configuration having more than one LED in each status indicator. The circuitry necessary for implementing a status indicator having more than one LED is known to one of ordinary skill in the art; therefore, such circuitry is not described in detail herein.

As shown in FIG. 5, the sensing device 250 capable of reading the visual display 110 comprises three optical sensors 214–216. Each optical sensor comprises an optical device 513 positioned for receiving light emitted from the optical device 512 of the corresponding status sensors 220–222. In addition, the optical device 513 channels the received light into a light-sensitive transistor 515. The light-sensitive transistor 515 activates a control circuit 516 that generates an electronic signal for communicating a changed state of the status indicators 220–222 to an external recipient such as the control unit 102. This embodiment accommodates the single LED status indicator configuration described above with reference to FIGS. 4A–4C. In another embodiment, the light-sensing transistor 515 may be configured to sense a narrow bandwidth of light to detect a specific color of light, such as green, red or other light emitted from a status indicator 220–222. This embodiment accommodates the multi-LED status indicator configuration described above with reference to FIGS. 4A–4C.

Figure 6:
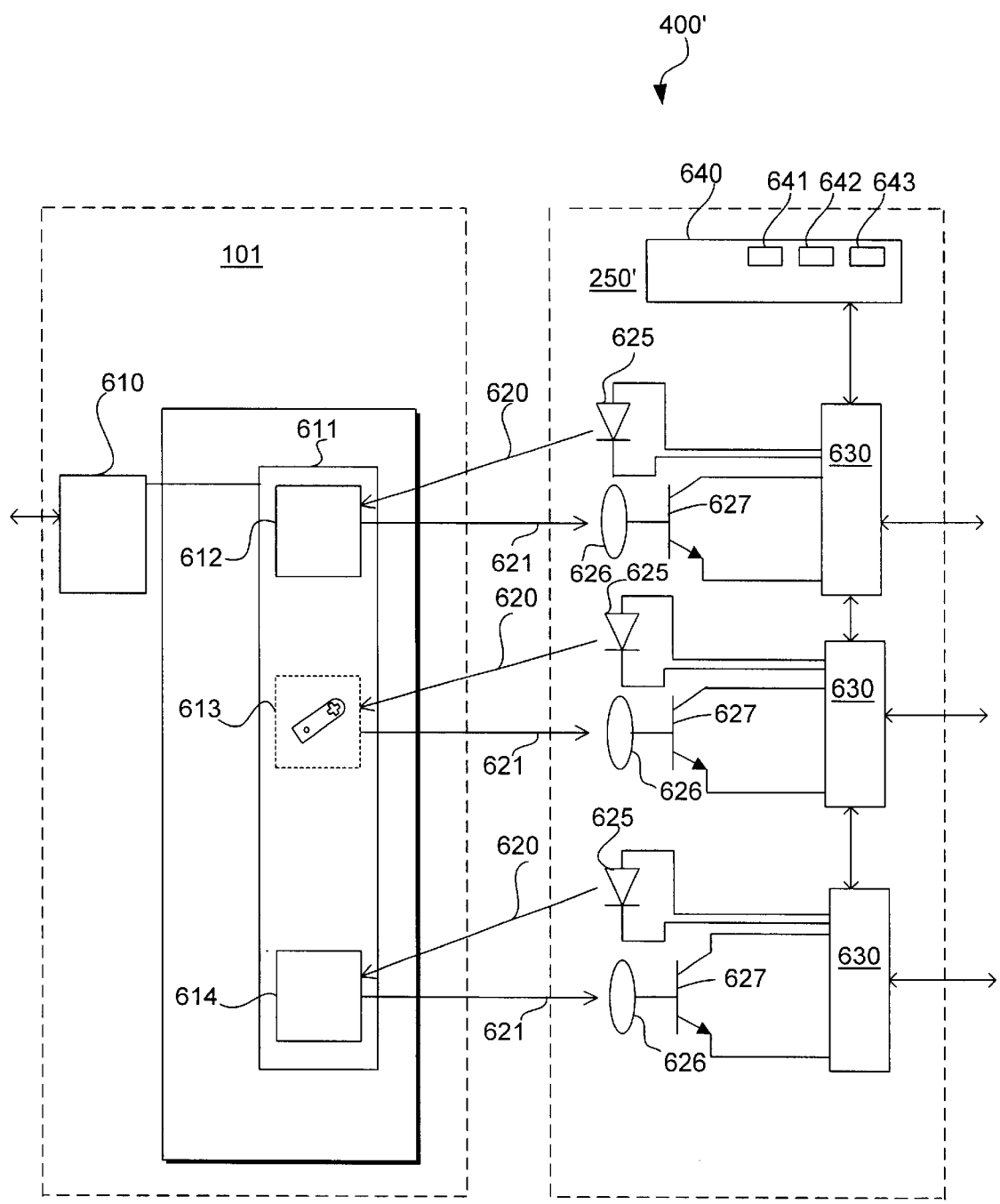
FIG. 6 is a block circuit diagram of one embodiment of a status sensing system configured for reading state changes of a liquid crystal display.

Referring now to FIG. 6, a block circuit diagram of sensing system 400' is shown. The block circuit diagram of FIG. 6 illustrates the sensing system 400' described above with reference to FIGS. 4D–4E. In addition, FIG. 6 illustrates a visual display 110 of a portable medical device 101' having a plurality of LCD status indicators 612–614. As shown in FIG. 6, sensing device 250' transmits a light source 620 from an LED 625 that illuminates the LCD status indicators of the visual display 110. The light source 620 creates reflected light 621 that is received by an optical lens 626 of a light sensitive transistor 627. This embodiment allows the sensing device 250' to determine state changes of the LCD status indicators 612–614, and communicate the state changes of the LCD status indicators to a controller 640 or any other external system.

FIG. 6 illustrates the major components of a visual display 110 and a sensing device 250' necessary for the implementation of the present invention. The following discussion is intended to describe one suitable environment in which the invention may be implemented. Therefore, those of ordinary skill in the art would appreciate that the visual display and the sensing device may include more components than those shown in FIG. 6.

Similar to the embodiment described above with reference to FIGS. 4D–4E, status indicators 612–614 of the sensing system 400' comprise an LCD display 611 that provides shading over a back plane having a painted icon. For instance, when the LCD is not activated, e.g., when the device has a low battery, the painted icon 613 on the back plane of the LCD display 611 is exposed. When the LCD of an individual status indicator is activated, the painted icon of the back plane is covered by a shaded block of the LCD, such as those shown in the first and third status indicators 612 and 614. In this embodiment, the activation or deactivation of the LCD of each status indicator may be configured to represent a particular status of the portable medical device 101.

As shown in FIG. 6, the LCD display 611 is also electronically coupled to a control circuit 610 for controlling the output of each status indicator 612–614. Accordingly, the control circuit 610 is electronically connected to the various components internal to the portable medical device 101 for sensing the status of the components, such as the battery level, maintenance schedule, etc. As described above, the control circuit 610 indicates a status change on one or more status indicators 612–614 when a status of a component changes.

As shown in FIG. 6, the sensing device 250' comprises a plurality of LED's 625 that produces a light source 620. Each LED 625 is configured such that the light source 620 is directed towards one status indicator. For example, the first status indicator 612 reflects the light source 620 to create a reflection 621 of the light that is directed towards an optical device 626 for capture. Accordingly, the optical device 626 directs the reflected light 621 into a light-sensitive transistor 627 for generating an electronic signal to a control circuit 630. As known to one of ordinary skill in the art, each optical device 626 may be made from an optical fiber, lens, or any like material for transferring and guiding the reflected light 621 into a light-sensitive transistor 627.

Also shown in FIG. 6, the control circuits 630 are configured for electronic communication with a remote system such as a control unit (102 of FIG. 1). Similar to the control circuit (516 of FIG. 5) described above, the control circuits 630 generate an electronic signal that communicates an alarm, audible sound, electronic text message, etc., to indicate a changed state of one or more status indicators. In addition, the control circuits 630 may be attached to an external light controller 640 for activating a plurality of lights 641–643, where each light 641–643 is configured to activate or deactivate in accordance to a corresponding status indicator 612–614. In accordance with one aspect of the present invention, it is preferred that the plurality of lights 641–643 of the external controller 640 are positioned in an area that allows the plurality of lights 641–643 to effectively communicate the device status changes to a user. In another embodiment, the external controller 640 may be configured to communicate a changed state of one or more status indicators by the turning on a light, generating an electric signal, creating an audible alarm, etc. In several illustrative examples, the external controller 640 may be connected to a mechanical buzzer, speaker system, piezo electric device, or any other like device for producing an audible alarm. In addition to the configurations described above, the status sensing systems (400 and 400') can be configured to determine the position of a portable medical device. In this embodiment, the status sensing systems can determine if a portable medical device has been deployed, stolen, moved, etc. In such an embodiment, the optical sensors can be used to detect any such activity by monitoring the presence or absence of a light source reflected or produced by the portable medical device. In another embodiment, a separate optical or mechanical sensor can be directly configured to the device to determine the presence or absence of the device. In yet another embodiment, an audible sensor can be configured to detect the presence or absence of the portable medical device by monitoring the presence or absence of an audible signals produced by the portable medical device.

As known to one of ordinary skill in the art, the internal circuitry of the control circuit 630 and external controller 640 can be implemented by the use of generally known solid-state electronic components. Although the sensing device 250' in this illustrative embodiment is configured to read three status indicators, one skilled in the art will appreciate that the sensing device 250' may be configured to sense more or less than three individual status indicators without departing from the spirit and scope of the present invention.

By the use of the above-described sensing device, status signals can readily be detected and communicated to a remote system, such as a control unit 102, without the need of a substantial hardware or software modification to the portable medical device 101. The sensing device may also translate specific status signals into electronic signals that control an alarm, speaker, or any other like device.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An apparatus for communicating status information of a portable medical device to a remote recipient, the apparatus comprising:
    a sensing device having a receiver for detecting a state change in a status indicator of the portable medical device, wherein the receiver is configured on the sensing device such that when the sensing device is positioned over the portable medical device the receiver is aligned to detect the state change in the status indicator of the portable medical device; and
    a circuit coupled to the receiver for communicating an electronic signal indicative of the detected state change of the status indicator to the remote recipient.

2. The apparatus of claim 1, wherein the receiver is an optical receiver configured to detect optical signals produced by the status indicator of the portable medical device.

3. The apparatus of claim 2, further comprising a light source for illuminating the status indicator, wherein the light source is configured to allow the optical receiver to detect a changed state of the status indicator.

4. The apparatus of claim 2, wherein the optical receiver and circuit are coupled to a housing that encloses the portable medical device.

5. The apparatus of claim 2, wherein the optical receiver and circuit are couplable to the portable medical device.

6. The apparatus of claim 2, wherein the optical receiver comprises a light-sensitive device configured for detecting the presence of a light source generated by the status indicator.

7. The apparatus of claim 2, wherein the optical receiver comprises a light-sensitive device configured for detecting the presence of a light source of a predetermined wavelength generated by the status indicator.

8. The apparatus of claim 1, wherein the receiver is configured for detecting audible signals produced by at least one status indicator of the portable medical device.

9. The apparatus of claim 8, wherein the circuit is configured to distinguish a particular status signal based on the duration of the audible signal.

10. The apparatus of claim 8, wherein the circuit is configured to distinguish a particular status signal based on the tone of the audible signal.

11. The apparatus of claim 8, wherein the circuit is configured to distinguish a particular status signal based on the volume of the audible signal.

12. The apparatus of claim 8, wherein the circuit is configured to determine a particular status signal based on a duration of time between repetitious audible signals.

13. The apparatus of claim 1, wherein the circuit and receiver are configured to determine movement of the portable medical device.

14. The apparatus of claim 1, wherein the circuit is configured to electronically communicate with a plurality of lights, wherein the plurality of lights are each activated or deactivated in response to a state change of at least one corresponding status indicator.

15. The apparatus of claim 1, wherein the circuit is configured to electronically communicate with at least one light, wherein the light is activated or deactivated in response to a state change of at least one status indicator.

16. The apparatus of claim 1, wherein the circuit is configured to electronically communicate with a speaker system, wherein the speaker system is configured to produce an audible tone when the circuit receives a corresponding signal indicating a state change of one corresponding status indicator.

17. The apparatus of claim 1, further comprising a plurality of receivers, each receiver corresponding to a different one of a plurality of status indicators of the portable medical device, and wherein at least two of the receivers are positioned such that when the apparatus is positioned over the portable medical device, the at least two receivers are aligned to receive status information from the corresponding status indicators.

18. The apparatus of claim 17 wherein a distance between the at least two receivers matches a distance between each of the corresponding status indicators.

19. A method for communicating status of a portable medical device to a remote recipient, wherein the method comprises:
    positioning a sensing device over the portable medical device such that a receiver of the sensing device is aligned with a visual display of the portable medical device;
    detecting with the receiver at least one state change in the visual display of the portable medical device, wherein the state change indicates the status of the portable medical device;
    generating an electronic signal indicative of the status of the portable medical device; and communicating the electronic signal to the remote recipient.

20. The method of claim 19, further comprising generating a visual alarm signal at the remote recipient in response to receiving the communicated electronic signal.

21. The method of claim 19, further comprising generating an audible alarm signal at the remote recipient in response to receiving the communicated electronic signal.

22. A system for communicating a status indicator signal from a portable medical device to a remote system, wherein the system comprises:

means for detecting at least one state change of one status indicator configured in the portable medical device, wherein the state change is indicative of a determined status of the portable medical device, and further wherein the means for detecting is configured such that when the means for detecting is positioned over the portable medical device, the means for detecting is aligned to detect the at least one state change;

means for generating an electronic signal indicative of the determined status of the portable medical device; and means for communicating the electronic signal to the remote system.

23. The system of claim 22, further comprising, means for generating a visual signal at the remote system in response to receiving the communicated electronic signal.

24. The system of claim 22, further comprising, means for generating an audible alarm signal at the remote system in response to receiving the communicated electronic signal.

25. The apparatus of claim 22, wherein the status indicator comprises a liquid crystal display configured to communicate an operational state of the portable medical device.

26. The system of claim 22, wherein the status indicator comprises an electronic light source configured to communicate an operational state of the portable medical device.

27. An apparatus for storing a portable medical device having at least one status indicator, the apparatus comprising:

a housing sized to receive the portable medical device;

a sensing device mounted in the housing, wherein the sensing device comprises:

at least one receiver positioned on the sensing means such that when the sensing means is positioned over the portable medical device the receiver is aligned to detect a state change in a status indicator of the portable medical device; and a circuit coupled to the receiver for communicating status information from at least one status indicator of the portable medical device.

28. The apparatus of claim 27, wherein the portable medical device comprises a plurality of status indicators, wherein the sensing device comprises a plurality of receivers, each receiver corresponding to a different one of the plurality of status indicators, and wherein at least one of the receivers are positioned on the sensing device such that when the sensing device is positioned over the portable medical device, the at least one receiver is aligned to receive status information from the corresponding one of die plurality of status indicators.

29. The apparatus of claim 27, wherein the receiver is an optical receiver configured to detect optical signals produced by the status indicator of the portable medical device.

30. The apparatus of claim 29, wherein the sensing device further comprises a light source for illuminating at least one status indicator of the portable medical device, wherein the illumination of the status indicator allows at least one optical receiver to determine a status from the status indicator.

31. The apparatus of claim 27, wherein the receiver is configured for detecting audible signals produced by at least one stains indicator of the portable medical device.

32. The apparatus of claim 31, wherein the circuit is configured to distinguish a particular status signal based on the duration of the audible signal.

33. The apparatus of claim 31, wherein the circuit is configured to distinguish a particular status signal based on the tone of the audible signal.

34. The apparatus of claim 31, wherein the circuit is configured to distinguish a particular status signal based on the volume of the audible signal.

35. The apparatus of claim 31, wherein the circuit is configured to determine a particular status signal based on a duration of time between repetitious audible signals.

36. The apparatus of claim 27, wherein the circuit is configured to electronically communicate with a plurality of lights, wherein the plurality of lights are each activated or deactivated in response to a state change of one corresponding status indicator.

37. The apparatus of claim 27, wherein the circuit is configured to electronically communicate with a plurality of lights, wherein the plurality of lights are each activated or deactivated in response to a state change of one corresponding status indicator.

38. The apparatus of claim 27, wherein the circuit is configured to electronically communicate with at least one light, wherein the light is activated or deactivated in response to a state change of one corresponding status indicator.

39. The apparatus of claim 27, wherein the circuit is configured to electronically communicate with a sound device, wherein the sound device is configured to produce an audible tone when the circuit receives a corresponding signal indicating a state change of one corresponding status indicator.

40. The apparatus of claim 39, wherein the sound device is a piezo electric device.

41. The apparatus of claim 39, wherein the sound device is a speaker system.

42. The apparatus of claim 39, wherein the sound device is a mechanical buzzer.

* * * * *

UNITED STATES PATENT AND TRADEMARK OFFICE
CERTIFICATE OF CORRECTION

PATENT NO.   : 6,727,814 B2
DATED        : April 27, 2004
INVENTOR(S)  : Saltzstein et al.

It is certified that error appears in the above-identified patent and that said Letters Patent is hereby corrected as shown below:

Column 12,
Line 47, "receivers arc" should read -- receivers are --

Column 13,
Line 25, "visual signal" should read -- visual alarm signal --

Column 14,
Line 3, "one of die" should read -- one of the --
Line 15, "one stains" should read -- one status --

Signed and Sealed this

Fifth Day of April, 2005

JON W. DUDAS
*Director of the United States Patent and Trademark Office*